United States Patent [19]

Hallinan et al.

[11] 4,204,991

[45] May 27, 1980

[54] SARCOSINE[1] DEHYDROALANINE[8] ANGIOTENSIN II DERIVATIVES

[75] Inventors: E. Ann Hallinan, Evanston; Robert H. Mazur, Deerfield, both of Ill.

[73] Assignee: G. D. Searle & Co., Skokie, Ill.

[21] Appl. No.: 39,025

[22] Filed: May 14, 1979

Related U.S. Application Data

[63] Continuation-in-part of Ser. No. 844,999, Oct. 25, 1977, abandoned.

[30] Foreign Application Priority Data

Oct. 24, 1978 [GB] United Kingdom ............... 41664/78

[51] Int. Cl.[2] ..................... C07C 103/52; H61K 37/00
[52] U.S. Cl. .............................. 260/112.5 R; 424/177
[58] Field of Search .................. 260/112.5 R; 424/177

[56] References Cited

U.S. PATENT DOCUMENTS

| | | | |
|---|---|---|---|
| 3,886,134 | 5/1975 | Sipos et al. ..................... | 260/112.5 R |
| 3,907,762 | 9/1975 | Regoli et al. .................. | 260/112.5 R |

FOREIGN PATENT DOCUMENTS

993865  7/1976  Canada ............................. 260/112.5 R

OTHER PUBLICATIONS

Regoli et al., Pharmacological Reviews 26, (2) pp. 84 & 98.

*Primary Examiner*—Delbert R. Phillips
*Attorney, Agent, or Firm*—Mary Jo Kanady

[57] ABSTRACT

The sarcosine[1] dehydroalanine[8] angiotensin II derivatives of the present invention are potent angiotensin blockers.

4 Claims, No Drawings

SARCOSINE[1] DEHYDROALANINE[8] ANGIOTENSIN II DERIVATIVES

SUMMARY OF THE INVENTION

This is a continuation-in-part of U.S. application Ser. No. 844,999, filed Oct. 25, 1977 and now abandoned.

The present invention relates to a group of angiotensin II derivatives of the structure

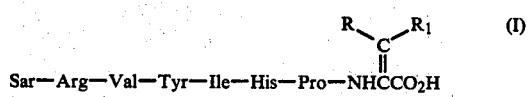

Sar—Arg—Val—Tyr—Ile—His—Pro—NHCCO$_2$H   (I)

wherein R is hydrogen or alkyl radical containing 1–4 carbon atoms; $R_1$ is hydrogen or an alkyl radical containing 1–4 carbon atoms; and the stereochemical configuration of each of the optically active amino acid residues is L or DL.

The abbreviations connote the amino acids defined in accordance with the nomenclature rules published by the IUPAC-IUB Commission on Biochemical Nomenclature, *Archives of Biochemistry and Biophysics*, 150, 1–8 (1972).

Preferred compounds of the present invention are those of formula (I) wherein all of the optically active amino acid residues are of the L-stereochemical configuration.

Also equivalent to the compounds of formula (I) for the purposes of this invention are the pharmaceutically acceptable acid addition salts thereof. Such acid addition salt can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gluconic, ascorbic and related acids.

DETAILED DESCRIPTION OF THE INVENTION

The compounds of the present invention resemble angiotensin II except for the unnatural amino acids at the N- and C- terminals. These compounds are pharmacological agents particularly useful as angiotensin inhibitors. Their inhibitory property is demonstrated in the following assay procedures:

Virgin female Charles River rats weighing 200–250 g. are injected 24 and 48 hours before use with diethyl stilbesterol, 1 mg./kg. subcutaneously, dissolved in corn oil. The rats are sacrificed by cervical dislocation and the uterus is removed and a section of the uterine horns mounted in a 2 ml. tissue bath containing a modified Tyrode solution maintained at 30° C. and bubbled with 95% oxygen, 5% carbon dioxide. A series of control contractions is elicited by alternate additions of angiotensin II, antidiuretic hormone (ADH) and bradykinin. A solution of the test compound is then substituted for the plain Tyrode solution and the treat contractions are obtained after an equilibration period of 15 or 30 minutes. Regularly timed contractions are elicited during the equilibration period in order to maintain the timed sequence of agonist additions. Three control and three treat contractions are averaged to obtain the mean percent change. The compound is rated active if it effects a significant decrease in the contractions produced by the action of the agonist.

Blood pressure is measured in Charles River albino rats anesthetized with pentobarbital sodium (50 mg./kg.) and pretreated with phenoxybenzamine (30 mg./kg.) and propranolol (15 mg./kg.) while maintaining body temperature at 32° C. The pressure is recorded from the carotid artery with a P-100 linear core pressure transducer, Physiograph. Both jugular veins are cannulated, one vein used for infusion of antagonists and the other for bolus injections of angiotensin II. An angiotensin II dose response curve is determined before each test of the antagonists so that each animal serves as its own control. An additional group of animals is tested to determine the effects of a 15-minute placebo infusion of saline on angiotensin II responses. After determination of the angiotensin II dose response curve, a placebo or inhibitor infusion is initiated and maintained for 15 minutes and continued during the second dose response. Immediately after the initial 15 minute infusion period the dose response curve is repeated. After the second dose response curve is obtained, the infusion of the antagonist is stopped. Thereafter, representation doses of angiotensin II which produced approximately 20–25 mm of mercury response in the control period are injected at 10–15 minute intervals until the control response is obtained. The time after infusion for the same response to appear is considered an indication of the antagonist's duration of activity. Relative activity is determined by comparing the ratio of the calculated doses obtained from the dose response curves of angiotensin II necessary to increase blood pressure 25 mm of mercury before and after the inhibitor.

The manufacture of the instant novel compounds is conveniently achieved by processes usually adapted to the synthesis of peptides. Thus, the C-terminal amino acid, optionally substituted with protecting groups, is coupled with the appropriate N-protected amino acid to afford the corresponding N-protected dipeptide. Removal of the N-protecting group is followed, similarly, by coupling with the N-protected amino acid required to produce the desired tripeptide. This sequential procedure is repeated until the desired octapeptide derivative is produced. Formation of the C-terminal $\alpha,\beta$-dehydro amino acid derivative, i.e. dehydroalanine, dehydrovaline, dehydroalkylalanine and dehydrodialkylalanine, may be accomplished before coupling, as exemplified in Example 22, or after coupling, as exemplified in Example 14.

The aforementioned coupling processes are preferably carried out in accordance with standard organic chemical techniques, whereby each intermediate peptide is produced as described hereinbefore and isolated prior to coupling with the next appropriate N-protected amino acid active ester. Alternatively, this sequential coupling process can be conducted by solid phase peptide synthesis, which consists of first attaching to a polymer support, e.g. chloromethylated copolystyrene-1% divinylbenzene polymer, the optionally N-protected C-terminal amino acid, followed by removal of the N-protecting group and coupling, in the presence of a suitable reagent, e.g. dicyclohexylcarbodiimide, successively with each of the appropriate N-protected amino acids.

The invention will appear more fully from the examples which follow. These examples are given by way of illustration only and are not to be construed as limiting the invention either in spirit or in scope, as many modifications both in materials and in methods will be apparent to those skilled in the art. In these examples temperatures are given in degrees Celsius, (°C.) and quantities of materials in parts by weight unless otherwise noted. The stereochemical configuration of each of the optically active amino acids in the examples is L or DL.

EXAMPLE 1

21.7 g of t-butoxycarbonylvaline is dissolved in 200 ml of methylene chloride. 22.2 ml of N-methylmorpholine is added to the solution. The solution is cooled to −70° C. 13.1 ml of isobutylchloroformate is then added. The reaction mixture is again cooled to −70° C. 23.2 g of tyrosine methyl ester hydrochloride is added to the reaction mixture. The reaction mixture is allowed to warm to room temperature, and then is stirred for 16 hours. The reaction mixture is extracted three times with 0.5 M potassium bisulfate and once with brine. The methylene chloride solution is dried over anhydrous sodium sulfate, filtered and stripped of solvent. The residue is dissolved in 200 ml of ethyl ether. The ether solution is added to cold rapidly stirring Skellysolve B. The white precipitate is filtered and dried to afford the product t-butoxycarbonylvalyltyrosine methyl ester.

EXAMPLE 2

29.6 g of t-butoxycarbonylvalyltyrosine methyl ester is dissolved in 255 ml of acetic acid. To this solution is added 128 ml of 6 N hydrochloric acid in dioxane. The reaction is allowed to stand for five minutes and the solution is removed under vacuum. The residue is triturated with ethyl ether. The resultant precipitate is filtered, washed with ethyl ether and dried in a vacuum oven at 55° C. to afford valyltyrosine methyl ester hydrochloride.

EXAMPLE 3

21.5 g of t-butoxycarbonylnitroarginine is dissolved in 200 ml of methylene chloride. 15.0 ml of N-methylmorpholine is added to the solution. The solution is cooled to −70° C. 8.8 ml of isobutyl chloroformate is then added. The reaction mixture is warmed up to −15° C. and stirred for 5 minutes. The reaction mixture is again cooled to −70° C. 22.3 g of valyltyrosine methyl ester hydrochloride is added to the reaction mixture. The reaction mixture is allowed to warm to room temperature, and then is stirred for 16 hours. The reaction mixture is extracted three times with 0.5 M potassium bisulfate and once with brine. The methylene chloride solution is dried over anhydrous sodium sulfate, filtered and stripped of solvent. The residue is dissolved in 200 ml of ethyl ether. The ether solution is added to cold rapidly stirring Skellysolve B. The white precipitate is filtered and dried to afford the product t-butoxycarbonylnitroarginylvalyltyrosine methyl ester.

EXAMPLE 4

30.9 g of t-butoxycarbonylnitroarginylvalyltyrosine methyl ester is dissolved in 177 ml of acetic acid. To this solution is added 88.5 ml of 6 N hydrochloric acid in dioxane. The reaction is allowed to stand for five minutes and the solvent is removed under vacuum. The residue is triturated with ethyl ether. The resultant precipitate is filtered, washed with ethyl ether and dried in a vacuum oven at 55° C. to afford nitroarginylvalyltyrosine methyl ester hydrochloride.

EXAMPLE 5

8.84 g of t-butoxycarbonylsarcosine is dissolved in 200 ml of methylene chloride. 10.5 ml of N-methylmorpholine is added to the solution. The solution is cooled to −70° C. 6.1 ml of isobutyl chloroformate is then added. The reaction mixture is warmed up to −15° C. and stirred for 5 minutes. The reaction mixture is again cooled to −70° C. 25.5 g of nitroarginylvalyltyrosine methyl ester hydrochloride is added to the reaction mixture. The reaction mixture is allowed to warm to room temperature, and then is stirred for 16 hours. The reaction mixture is extracted three times with 0.5 M potassium bisulfate and once with brine. The methylene chloride solution is dried over anhydrous sodium sulfate, filtered and stripped of solvent. The residue is dissolved in 200 ml of ethyl ether. The ether solution is added to cold rapidly stirring Skellysolve B. The white precipitate is filtered and dried to afford the product t-butoxycarbonylsarcosylnitroarginylvalyltyrosine methyl ester.

EXAMPLE 6

10.0 g of t-butoxycarbonylsarcosylnitroarginylvalyltyrosine methyl ester is dissolved in 30 ml of methanol. To this solution is added 60 ml of 1 N lithium hydroxide. The reaction mixture is stirred for three hours, then neutralized with 1 N hydrochloric acid to pH 7. The solvent is removed by vacuum and the residue is dissolved in N,N-dimethylformamide. The solution is filtered and the solvent removed by vacuum. The residue is dissolved in methanol/2-propanol. The alcohol solution is added to 1 liter of cold rapidly stirring ethyl ether. The white precipitate is filtered and dried in vacuo to afford t-butoxycarbonylsarcosylnitroarginylvalyltyrosine.

EXAMPLE 7

21.5 g of t-butoxycarbonylproline is dissolved in 200 ml of methylene chloride. 22.2 ml of N-methylmorpholine is added to the solution. The solution is cooled to −70° C. 13.1 ml of isobutyl chloroformate is then added. The reaction mixture is warmed up to −15° C. and stirred for 5 minutes. The reaction mixture is again cooled to −70° C. 15.6 g of serine methyl ester hydrochloride is added to the reaction mixture. The reaction mixture is allowed to warm to room temperature, and then stirred for 16 hours. The reaction mixture is extracted three times with 0.5 M potassium bisulfate and once with brine. The methylene chloride solution is dried over anhydrous sodium sulfate, filtered and stripped of solvent. The residue is dissolved in 200 ml of ethyl ether. The ether solution is added to cold rapidly stirring Skellysolve B. The white precipitate is filtered and dried to afford the product t-butoxycarbonylprolylserine methyl ester.

EXAMPLE 8

24.4 g of t-butoxycarbonylprolylserine methyl ester is dissolved in 262 ml of dioxane. To this solution is added 141 ml of 6 N hydrochloric acid in dioxane. The reaction is allowed to stand for ten minutes and the solvent is removed under vacuum. The residue is triturated with ethyl ether. The resultant product, prolylserine methyl ester hydrochloride, was a clear glass.

EXAMPLE 9

23.3 of t-butoxycarbonylisoleucine is dissolved in 200 ml of methylene chloride. 33.3 ml of N-methylmorpholine is added to the solution. The solution is cooled to −70° C. 13.1 ml of isobutylchloroformate is then added. The reaction mixture is warmed up to −15° C. and stirred for 5 minutes. The reaction mixture is again cooled to −70° C. 26.0 g of histidine methyl ester dihydrochloride is added to the reaction mixture. The reaction mixture is allowed to warm to room temperature, and then is stirred for 16 hours. The reaction mixture is extracted three times with 0.5 M potassium bisulfate and once with brine. The methylene chloride solution is dried over anhydrous sodium sulfate, filtered and stripped of of solvent. The residue is dissolved in 200 ml of ethyl ether. The ether solution is added to cold rapidly stirring Skellysolve B. The white precipitate is filtered and dried to afford the product t-butoxycarbonylisoleucylhistidine methyl ester.

EXAMPLE 10

29.4 g of t-butoxycarbonylisoleucylhistidine methyl ester is dissolved in 150 ml of methanol. To this solution is added 308 ml of 1 N lithium hydroxide. The reaction mixture is stirred for three hours, then neutralized with 1 N hydrochloride acid to pH 3. The solvent is removed by vacuum and the residue is dissolved in N,N-dimethylformamide. The solution is filtered and the solvent removed by vacuum. The residue is dissolved in methanol/2-propanol. The alcohol solution is added to 2 liters of cold rapidly stirring ethyl ether. The white precipitate is filtered and dried in vacuo to afford t-butoxycarbonylisoleucylhistidine hydrochloride.

EXAMPLE 11

10.1 g of t-butoxycarbonylisoleucylhistidine hydrochloride and 6.3 g of prolylserine methyl ester hydrochloride are dissolved in 100 ml of dimethylformamide. The solution is cooled to 0° C. To the solution is added 3.4 g of 1-hydroxybenzotriazole, 2.8 ml of N-methylmorpholine and 7.6 g of dicyclohexylcarbodiimide. The reaction mixture is stirred for two hours at 0° C. and then is allowed to stand at 4° C. for sixteen hours. Dicyclohexylurea is filtered from the reaction mixture and is washed with acetone. 300 ml of ethyl acetate is added to the solution. The solution is extracted three times with 300 ml saturated potassium bicarbonate and two times with 300 ml of brine. The product is extracted into 300 ml of 2 M potassium bisulfate. The acidic solution is neutralized with potassium carbonate. The slightly basic aqueous solution is extracted three times with 300 ml of methylene chloride. The methylene chloride solution, which contains the product, is dried over sodium sulfate, filtered and stripped of solvent under vacuum. The residue is dissolved in 100 ml of ethyl acetate. The solution is added to 1 liter of cold rapidly stirring Skellysolve B. The white precipitate was filtered and dried under vacuum at 55° C. to afford the product t-butoxycarbonylisoleucylhistidylprolylserine methyl ester.

EXAMPLE 12

8.5 g of t-butoxycarbonylisoleucylhistidylprolylserine methyl ester is dissolved in 51 ml of dioxane. To this solution is added 25.5 ml of 6 N hydrochloric acid in dioxane. The reaction is allowed to stand for ten minutes and the solvent is removed under vacuum to afford isoleucylhistidylprolylserine methyl ester hydrochloride.

EXAMPLE 13

9.8 g of t-butoxycarbonylsarcosylnitroarginylvalyltyrosine and 7.6 g of isoleucylhistidylprolylserine methyl ester hydrochloride are dissolved in 100 ml of dimethylformamide. The solution is cooled to 0° C. To the solution is added 2.03 g of 1-hydroxybenzotriazole, 1.7 ml of N-methylmorpholine and 4.64 g of dicyclohexylcarbodiimide. The reaction mixture is stirred for two hours at 0° C. and then is allowed to stand at 4° C. for sixteen hours. Dicyclohexylurea is filtered from the reaction mixture and is washed with acetone. 300 ml of ethyl acetate is added to the solution. The solution is extracted three times with 300 ml saturated potassium bicarbonate and two times with 300 ml of brine. The product is extracted into 300 ml of 2 M potassium bisulfate. The acidic solution is neutralized with potassium carbonate. The slightly basic aqueous solution is extracted three times with 300 ml of methylene chloride. The methylene chloride solution, which contains the product, is dried over sodium sulfate, filtered and stripped of solvent under vacuum. The residue is dissolved in 100 ml of ethyl acetate. The solution is added to 1 liter of cold rapidly stirring Skellysolve B. The white precipitate was filtered and dried under vacuum at 55° C. to afford the product t-butoxycarbonylsarcosylnitroarginylvalyltyrosylisoleucylhistidylprolylserine methyl ester.

EXAMPLE 14

3.0 g of t-butoxycarbonylsarcosylnitroarginylvalyltyrosylisoleucylhistidylprolylserine methyl ester is dissolved in 20 ml of pyridine and 10 ml of triethylamine. The solution is cooled in an ice bath. 0.51 g of tosyl chloride is added to the solution. At ten minute intervals, three additional 0.51 g batches of tosyl chloride are added. After standing for two hours, the reaction mixture is filtered. 200 ml of methylene chloride is added to the reaction. The solution is extracted three times with 5% ammonium hydroxide in water. The solution is then dried over sodium sulfate and stripped under vacuum. The residue istaken up in 2% methanol/methylene chloride and passed through a silica gel column to remove the colored impurities and afford the pure product t-butoxycarbonylsarcosylnitroarginylvalyltyrosylisoleucylhistidylprolyldehydroalanine methyl ester.

EXAMPLE 15

2.09 g of t-butoxycarbonylsarcosylnitroarginylvalyltyrosylisoleucylhistidylprolyldehydroalanine methyl ester is dissolved in 30 ml of dioxane. To this solution is added 60 ml of 1 N lithium hydroxide. The reaction mixture is stirred for three hours, then neutralized with 1 N hydrochloric acid to pH 7. The solvent is removed by vacuum and the residue is dissolved in N,N-dimethylformamide. Ths solution is filtered and the solvent removed by vacuum. The residue is dissolved in dioxane and added to 300 ml of cold rapidly stirring ethyl ether. The precipate is filtered and dried in vacuo to afford t-butoxycarbonylsarcosylnitroarginylvalyltyrosylisoleucylhistidylprolyldehydroalanine.

EXAMPLE 16

1.07 g of t-butoxycarbonylsarcosylnitroarginylvalyltyrosylisoleucylhistidylprolyldehydroalanine is stirred for thirty minutes at 0° C. in 10 ml of hydrogen fluoride and 1 ml of anisole. The crude product is run in a countercurrent distribution system of n-butanol:acetic acid:water (4:1:5) for 200 transfers. The solvent is removed under vacuum. The residue is dissolved in water and lyophilized to afford the product sarcosylarginylvalyltyrosylisoleucylhistidylprolyldehydroalanine diacetic acid salt which is represented by the formula

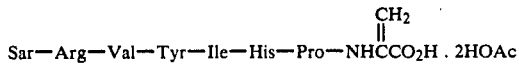

Sar—Arg—Val—Tyr—Ile—His—Pro—NHCHCO$_2$H . 2HOAc

EXAMPLE 17

2-Phenyl-4-isopropylidene-5-oxazolinone and other 2-phenyl-4-alkylidene-5-oxazolinones are prepared according to the method described in E. Baltazzi, et. al., Chemistry and Industry, Feb. 13, 1954, p. 191. 4.6 g of sodium metal are added to 1200 ml of methanol. The sodium is allowed to react with the methanol, then 149 g of benzyl mercaptan are added followed by 201 g of 2-phenyl-4-isopropylidene-5-oxazolinone. The reaction mixture is stirred for six hours then neutralized to pH5 with glacial acetic acid. The methanol is removed under vacuum. The residue is subjected to column chromatography on silica gel in 50% hexane-50% chloroform to remove the excess benzyl mercaptan. This affords pure product, methyl N-benzoyl-S-benzylpenicillaminate.

EXAMPLE 18

1000 ml of concentrated hydrochloric acid, 1000 ml of 90% formic acid and 1000 ml of distilled water are added to 286 g methyl N-benzoyl-S-benzylpenicillaminate. The reaction mixture is refluxed for forty-eight hours. The solvents are removed under vacuum, and residue is washed copiously with hot diethyl ether. The resultant precipitate is pure product, S-benzylpenicillamine hydrochloride.

EXAMPLE 19

1000 ml of methanol are cooled to −20° C. To this is added dropwise 171 g of thionyl chloride. After the thionyl chloride has been added, 199 g of S-benzylpenicilamine hydrochloride are added. The reaction mixture is refluxed for sixteen hours. The methanol is removed under vacuum. Fresh methanol is added to the reaction mixture then removed under vacuum. The residue is triturated with diethyl ether. The precipitate is filtered and washed with diethyl ether. This results in pure product, methyl S-benzylpencillaminate hydrochloride.

EXAMPLE 20

146 g of t-butoxycarbonyl proline are dissolved in 1500 ml of methylene chloride. 150 ml of N-methylmorpholine are added to the solution. The solution is cooled to −70° C. 89 ml of isobutylchloroformate are added. The reaction mixture is warmed to −15° C. and then cooled to −70° C. 197 g of methyl S-benzylpenicillaminate hydrochloride are added to the reaction mixture. The reaction mixture is stirred for sixteen hours at room temperature. The reaction mixture is extracted three times with 1.0 M potassium bisulfate and once with brine. The methylene chloride solution is dried over anhydrous sodium sulfate, filtered and stripped of solvent. The residue is dissolved in a minimum of diethyl ether. The ether solution is added to cold rapidly stirring hexane. The white precipitate is filtered and dried to afford the product, methyl t-butoxycarbonylprolylpenicillaminate.

EXAMPLE 21

230 g of methyl t-butoxycarbonylprolylpenicillaminate are dissolved in 1000 ml methylene chloride. 167 g of metyl trifluoromethylsulfonate are added to the solution. The reaction mixture is stirred for six hours. 500 ml of ethanol was added to the reaction mixture. The solvents are removed from the reaction under vacuum.

The residue is dissolved in 1000 ml of methylene chloride. 142 ml of triethylamine are added to the solution. The reaction mixture is allowed to stand for two hours. The solvent is removed under vacuum. The residue is subjected to column chromatography on silica gel in 20% hexane-80% chloroform. This afforded pure product, methyl t-butoxycarbonylprolyl-2,3-dehydrovalinate.

EXAMPLE 22

16.3 g of methyl t-butoxycarbonylprolyl-2,3-dehydrovalinate are dissolved in 100 ml of methanol. 150 ml of 1 M sodium hydroxide are added to the solution. The solution is stirred for six hours. The solution is neutralized to pH3 with 1 M potassium bisulfate. The solvent is removed under vacuum. The residue is dissolved in ethyl acetate. The inorganic salts are filtered from the ethyl acetate solution. The ethyl acetate is removed under vacuum to yield the product, t-butoxycarbonylprolyl-2,3-dehydrovaline.

EXAMPLE 23

1.2 g of t-butoxycarbonylprolyl-2,3-dehydrovaline are dissolved in 70 ml of dimethylformamide. 0.62 g of cesium carbonate and 10 g of chloromethylated polystyrene 2% divinylbenzene resin (0.35 milliequivalents/gram) are added to the solution. The reaction mixture is stirred for thirty-six hours at 60° C. The resin is filtered and washed with dimethylformamide, water, 2-propanol, and methylene chloride. The resin is dried at 70° C. under vacuum to yield the dipeptide t-butoxycarbonylprolyl-2,3-dehydrovaline which is attached to the resin by a benzyl ester linkage.

EXAMPLE 24

To attach t-butoxycarbonyl-im-tosylhistidine to the butoxycarbonylprolyl-2,3-dehydrovaline resin and add the subsequent amino acids to obtain the desired peptide the following sequence is repeated for each amino acid on an automated peptide synthesizer.

The t-butoxycarbonyl protecting group of 10 g of t-butoxyprolyl-2,3-dehydrovalyl resin is removed with 40% trifluoroacetic acid-60% methylene chloride. This resin is treated twice with the acid solution to ensure the removal of the t-butoxycarbonyl group. The excess acid is rinsed off with methylene chloride followed by 2-propanol and the sequence of rinsing with methylene chloride followed by 2-propanol is repeated several times.

The trifluoroacetate salt of the peptide resin is neutralized with N,N-diisopropylethyl amine. The excess amine is rinsed off with methylene chloride followed by 2-propanol as above.

The deblocked peptide resin has attached to it t-butoxycarbonyl-im-tosylhistidine via dicyclohexylcarbodiimide. t-Butoxycarbonyl-im-tosylhistidine and dicyclohexylcarbodiimide are added in two-fold excess. 2.86 g of t-butoxycarbonyl-im-tosylhistidine dissolved in 25 ml of methylene chloride and 1.46 g of dicyclohexylcarbodiimide dissolved in 25 ml methylene chloride are added to the resin. The reaction is agitated for two hours. The coupling is repeated. The resin is rinsed as before with methylene chloride followed by 2-propanol. The resin is acetylated two times with 0.4 M acetic anhydride in methylene chloride. The resin is rinsed as before with methylene chloride followed by 2-propanol.

The above sequence is repeated for the addition of each amino acid until the desired peptide, t-butoxycarbonylsarcosyl-N$^G$-nitroarginylvalyl-O-2-bromobenzyloxycarbonyltyrosylisoleucyl-im-tosylhistidylprolyl-2,3-dehydrovalyl resin is obtained.

EXAMPLE 25

100 ml of liquid hydrogen fluoride is added to 10 g of the protected peptide resin from the previous example in 10 ml of anisole. The reaction is stirred for twenty minutes at 4° C. The hydrogen fluoride is removed under water aspirator vacuum with a stream of nitrogen gas. The resin is washed with diethyl ether to remove the anisole. The resin is then washed three times with 25 ml of distilled water. The water is removed from the product under vacuum. The residue is subjected to column chromatography on silica gel which has been modified with octadecyltrichlorosilane. This affords pure product, sarcosylarginylvalyltyrosylisoleucylhistidylprolyl-2,3-dehydrovaline which is represented by the formula $$\text{Sar—Arg—Val—Tyr—Ile—His—Pro—NH}\underset{\underset{\overset{\|}{\text{C}}}{}}{\overset{\text{H}_3\text{C}\diagdown\diagup\text{CH}_3}{}}\text{COOH}$$

EXAMPLE 26

Substitution of 2-phenyl-4-methylene-5-oxazolinone for the 2-phenyl-4-isopropylidine-5-oxazolinone in Example 17 and substantial repetition of the procedures described in Examples 17 through 25 gives sarcosylarginylvalyltyrosylisoleucylhistidylprolyldehydroalanine.

Substitution of 2-phenyl-4-isobutylidine-5-oxazolinone for the 2-phenyl-4-isopropylidine-5-oxizolinone in Example 17 and substantial repetition of the procedures described in Example 17 through 25 gives sarcosylarginylvalyltyrosylisoleucylhistidylprolyldehydroisoleucine which is represented by the formula $$\text{Sar—Arg—Val—Tyr—Ile—His—Pro—NH}\underset{\underset{\overset{\|}{\text{C}}}{}}{\overset{\text{H}_3\text{C}\diagdown\diagup\text{CH}_2\text{CH}_3}{}}\text{COOH}$$

EXAMPLE 27

21.5 g of t-butoxycarbonylproline are dissolved in 500 ml of methylene chloride. The solution is cooled to −70° C. 20.2 g of N-methylmorpholine are added, followed by the addition of 13.7 g of isobutylchloroformate. The reaction mixture is warmed up to −15° C. and again cooled to −70° C. 15.6 g of methyl serinate hydrochloride are added to the reaction mixture which is stirred for sixteen hours at room temperature. The reaction mixture is extracted three times with 1 M potassium bisulfate, three times with a saturated solution of potassium bicarbonate and two times with brine. The methylene chloride solution is dried over anhydrous sodium sulfate, filtered and stripped of solvent. The product is purified by chromatography on silica gel to give methyl t-butoxycarbonylprolylserinate.

EXAMPLE 28

31.6 g of methyl t-butoxycarbonylprolylserinate are dissolved in 300 ml methylene chloride. 20.2 g of N-methylmorpholine are added to the solution followed by the addition of 19.1 g toluenesulfonyl chloride. The reaction mixture is chromatographed on silica gel to obtain pure product, methyl t-butoxycarbonylprolyldehydroalaninate.

EXAMPLE 29

29.8 g of methyl t-butoxycarbonylprolydehydroalaninate are dissolved in 300 ml dioxane. 300 ml of 1 N sodium hydroxide are added. The reaction is stirred for two hours. The reaction mixture is extracted one time with diethyl ether. It is neutralized with 1 M potassium bisulfate to pH5. The solvent is stripped from the product. The residue is dissolved in acetonitrile and the salts are filtered from the solution. The acetonitrile is stripped from the product. Traces of solvent are removed under high vacuum which yields pure product, t-butoxycarbonylprolyldehydroalanine.

Substitution of t-butoxycarbonylprolyldehydroalanine for the t-butoxycarbonylprolyl-2,3-dehydrovaline of Example 23 and substantial repetition of the procedures described in Examples 23 through 25 provides sarcosylarginylvalyltyrosylisoleucylhistidylprolyldehydroalanine which is represented by the formula $$\text{Sar—Arg—Val—Tyr—Ile—His—Pro—NH}\underset{\underset{\overset{\|}{\text{C}}}{}}{\overset{\text{CH}_2}{}}\text{COOH}$$

What we claim is:

1. Compounds of the formula $$\text{Sar—Arg—Val—Tyr—Ile—His—Pro—NH}\underset{\underset{\overset{\|}{\text{C}}}{}}{\overset{\text{R}\diagdown\diagup\text{R}_1}{}}\text{CO}_2\text{H}$$

wherein R is hydrogen or an alkyl radical containing 1–4 carbon atoms; R$_1$ is hydrogen or an alkyl radical containing 1–4 carbon atoms; and the stereochemical configuration of each of the optically active amino acid residues is L or DL.

2. The compound according to claim 1 which is sarcosylarginylvalyltyrosylisoleucylhistidylprolyldehydroalanine.

3. The compound according to claim 1 which is sarcosylarginylvalyltyrosylisoleucylhistidylprolyldehydrovaline.

4. The compounds according to claim 1 wherein the stereochemical configuration of all of the optically active amino acid residues is L.

* * * * *